(12) United States Patent
Chen et al.

(10) Patent No.: US 8,377,867 B2
(45) Date of Patent: Feb. 19, 2013

(54) USE OF EPINECIDIN-1 PEPTIDES AND ANTI-LIPOPOLYSACCHARIDE FACTOR PEPTIDES FOR TREATING MICROBIAL INFECTION

(75) Inventors: Jyh-Yih Chen, Ilan (TW); Chia-Yu Pan, Ilan (TW)

(73) Assignee: Academia Sinica, Taipei (TW)

( * ) Notice: Subject to any disclaimer, the term of this patent is extended or adjusted under 35 U.S.C. 154(b) by 359 days.

(21) Appl. No.: 12/685,085

(22) Filed: Jan. 11, 2010

(65) Prior Publication Data

US 2010/0184647 A1     Jul. 22, 2010

Related U.S. Application Data

(60) Provisional application No. 61/143,476, filed on Jan. 9, 2009.

(51) Int. Cl.
    *A61K 38/16*   (2006.01)
    *A61K 38/12*   (2006.01)
    *A61P 31/04*   (2006.01)

(52) U.S. Cl. ............ 514/1.1; 514/1.4; 514/2.1; 514/2.2; 514/4.6; 514/21.4

(58) Field of Classification Search ........................ None
    See application file for complete search history.

(56) References Cited

U.S. PATENT DOCUMENTS 5,994,306 A * 11/1999 Chang et al. .................. 514/2.1
6,255,282 B1 * 7/2001 Jaynes ....................... 424/184.1

OTHER PUBLICATIONS

Yin, Aquaculture, 2006.*
Pan, DNA and Cell Biology, 26, 2007.*
Mutwiri, J Parasitology, 86, 6, 2000.*
McInturff, J Investigative Dermatology, 125, 2005.*
Pan, International Immunophaemacology, 7, 2007.*
Pan et al., "In Vitro Activities of Three Synthetic Peptides Derived from Epinecidin-1 and an Anti-Lipopolysaccharide Factor Against Propionibacterium Acnes, *Candida albicans*, and *Trichomonas vaginalis*", *Peptides*, vol. 30, pp. 1058-1068 (2009).
Pan et al., "Shrimp (*Penaeus monodon*) Anti-Lipopolysaccharide Factor reduces the Lethality of *Pseudomonas aeruginosa* Sepsis in Mice", *International Immunopharmacology*, vol. 7, pp. 687-700 (2007).
Somboonwiwat et al., "Recombinant Expression and Anti-Microbial Activity of Anti-Lipopolysaccharide Factor (ALF) from the Black Tiger Shrimp *Penaeus monodon*", *Developmental & Comparitive Immunology*, vol. 29, pp. 841-851 (2005).
Pan et al., "Gene Expression and Localization of the Epinecidin-1 Antimicrobial Peptide in the Grouper (*Epinephelus coioides*), and its Role in Protecting Fish Against Pathogenic Infection", *DNA and Cell Biology*, vol. 26, No. 6, pp. 403-413 (2007).
Mutwiri et al., "Effect of the Antimicrobial Peptide, D-Hecate, on Trichomonads", *The Journal of Parasitology*, vol. 86, No. 6, pp. 1355-1359 (2000).

* cited by examiner

*Primary Examiner* — Robert A Wax
*Assistant Examiner* — William Craigo
(74) *Attorney, Agent, or Firm* — Occhiuti Rohlicek & Tsao LLP

(57) ABSTRACT

Treatments of trichomonas, propionibacterium, or yeast infection using an epinecidin-1 peptide or an anti-lipopolysaccharide factor peptide.

12 Claims, No Drawings

USE OF EPINECIDIN-1 PEPTIDES AND ANTI-LIPOPOLYSACCHARIDE FACTOR PEPTIDES FOR TREATING MICROBIAL INFECTION

RELATED APPLICATION

This application claims priority to U.S. Provisional Application No. 61/143,476, filed on Jan. 9, 2009, the content of which is hereby incorporated by reference in its entirety.

BACKGROUND OF THE INVENTION

Antimicrobial peptides (AMPs) are broad spectrum antibiotics produced by eukaryotic organisms (e.g., fish and shrimp) to fight against infections caused by bacteria, viruses, or fungi.

Epinecidin-1, an AMP found in groupers, and anti-lipopolysaccharide factors (ALFs), an AMP subfamily found in, e.g., shrimps, protect these aquatic animals against microbial infections.

SUMMARY OF THE INVENTION

The present invention is based on two unexpected discoveries: (1) a fragment of grouper Epinecidin-1, i.e., Epinecidin-$1_{22-42}$ (GFIFHIIKGLFHAGKMIHGLV; SEQ ID NO:1), inhibits growth of *Propionibacterium acnes*, *Candida albicans*, and *Trichomonas vaginalis*, and (2) a fragment of shrimp ALF, i.e., $SALF_{55-76}$ (ECKFTVKPYLKRFQVYYKGRMWCP; SEQ ID NO:2), inhibits growth of *T. vaginalis*.

Accordingly, one aspect of this invention relates to a method for treating infection with a trichomonas (e.g., *T. vaginalis*) by administering to a subject in need thereof an effective amount of an epinecidin-1 peptide or an ALF peptide. In one example, the epinecidin-1 peptide includes the amino acid sequence of SEQ ID NO:1 and the ALF peptide, either linear or cyclic, includes the amino acid sequences of SEQ ID NO:2.

Another aspect of this invention features treating infection with a propionibacterium (e.g., *P. acnes*) or yeast (e.g., *Candida albicans*) using an epinecidin-1 peptide.

The term "treating" as used herein refers to the application or administration of a composition including one or more active agents to a subject, who has any of the infections mentioned above, a symptom of the infection, or a predisposition toward the infection, with the purpose to cure, heal, alleviate, relieve, alter, remedy, ameliorate, improve, or affect the infection, the symptoms of the infection, or the predisposition toward the infection. "An effective amount" as used herein refers to the amount of each active agent required to confer therapeutic effect on the subject, either alone or in combination with one or more other active agents. Effective amounts vary, as recognized by those skilled in the art, depending on route of administration, excipient choice, and co-usage with other active agents.

Also within the scope of this invention is the use of any of the peptides mentioned above for the manufacture of a medicament for treating trichomonas, propionibacterium, or yeast infection.

The details of one or more embodiments of the invention are set forth in the description below. Other features or advantages of the present invention will be apparent from the following detailed description of several embodiments and also from the appended claims.

DETAILED DESCRIPTION OF THE INVENTION

Disclosed herein is a method of treating trichomonas, propionibacterium, or yeast infection using an epinecidin-1 peptide or an ALF peptide, or a DNA plasmid for expressing either peptide. The term "epinecidin-1 peptide" used herein refers to a peptide including an amino acid sequence at least 80% (e.g., 85%, 90%, or 95%) identical to GFIFHIIKGLFHAGKMIHGLV (Epinecidin-$1_{22-42}$, SEQ ID NO:1). The term "ALF peptide" used herein refers to a peptide including an amino acid sequence at least 80% (e.g., 85%, 90%, or 95%) identical to ECKFTVKPYLKRFQVYYKGRMWCP ($SALF_{55-76}$; SEQ ID NO:2). A peptide, either linear or cyclic, refers to a polymer composed of up to 150 amino acid monomers. Preferably, the epinecidin-1 peptide used to practice the methods of this invention contains up to 80 amino acids (e.g., up to 50 or 30 amino acids) and the ALF peptide used in this invention contains up to 130 amino acids (e.g., up to 50 or 30 amino acids). An epinecidin-1 peptide can be a variant of Epinecidin-$1_{22-42}$ that contains one or more conservative mutations in SEQ ID NO:1. An ALF peptide can be a variant of $SALF_{55-76}$ that contains one or more conservative mutations in SEQ ID NO:2. In a conservative mutation, the replacement amino acid residue has structural or chemical characteristics similar to those of the replaced amino acid residue.

Percent homology of two amino acid sequences can be determined using the algorithm described in Karlin and Altschul, *Proc, Natl. Acad. Sci. USA* 87:2264-2268, 1990, modified as described in Karlin and Altschul, *Proc, Natl. Acad. Sci. USA* 90:5873-5877, 1993. Such an algorithm is incorporated into the NBLAST and XBLAST programs of Altschul et al., *J. Mol. Biol.* 215:403-410, 1990. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al., *Nucleic Acids Res.* 25:3389-3402, 1997. When utilizing the BLAST and Gapped BLAST programs, the default parameters of the respective programs (e.g., XBLAST and NBLAST) are used. See www.ncbi.nlm.nih.gov.

A DNA plasmid for expressing either an epinecidin-1 peptide or an ALF peptide described above includes a suitable promoter operably linked to a nucleotide sequence coding for either peptide. As used herein, the term "promoter" refers to a nucleotide sequence containing elements that initiate the transcription of an operably linked nucleic acid sequence in cells of the subject to be treated in the method of this invention. At a minimum, a promoter contains an RNA polymerase binding site. It can further contain one or more enhancer elements which, by definition, enhance transcription, or one or more regulatory elements that control the on/off status of the promoter.

The epinecidin-1 peptides, ALF peptides, and DNA plasmids for expressing such can be prepared by conventional methods. For example, an epinecidin-1 or ALF peptide, in linear form, can be prepared by chemical synthesis or recombinant technology. To make a cyclic peptide, two functional groups each can be added to one of the N-terminus and C-terminus of a linear peptide (e.g., an acetyl group and an amide group added to the N- and C-termini, respectively) and the two functional groups can then form a covalent bond, thereby producing a cyclic molecule.

Any of the epinecidin-1 peptides, ALF peptides, or DNA plasmids for expressing such can be mixed with a pharmaceutically acceptable carrier to form pharmaceutical compositions for use in treating infection caused by trichomonas, propionibacterium, or yeast in a subject (e.g., a human) suffering from or at risk for the infection. An "acceptable carrier" is a carrier compatible with the active ingredient of the composition (and preferably, stabilizes the active ingredient) and not deleterious to the subject to be treated. Suitable carriers include, but are not limited to, microcrystalline cellulose, mannitol, glucose, defatted milk powder, polyvinylpyrrolidone, and starch, or a combination thereof To practice the method provided in this application, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. When a DNA plasmid expressing an epinecidin-1 or ALF peptide is used, it can be delivered via a microbial vector, such as *Salmonella*, BCG, adenovirus, poxvirus, or vaccinia.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. A peptide- or DNA plasmid-containing composition can also be administered in the form of suppositories for rectal administration.

To practice the method provided in this application, any of the epinecidin-1 peptides or ALF peptides can be formulated in a personal hygiene product for use upon the skin of a person to reduce the risk of infection or prevent spread of infection. Exemplary personal hygiene products include, but are not limited to, soap (preferably in liquid form), shampoo, mouth wash, vaginal solution, cleansing pad, deodorant, and facial tissue. Methods for making such a personal hygiene product are well known in the hygiene product industry. In one example, the personal hygiene product described herein is prepared by mixing an epinecidin-1 peptide or ALF peptide with a commercially available personal hygiene product, e.g., the vaginal solution provided by Tien Liang Biotech Co. Ltd, Taiwan, and the Yu-Jie-Ning body shampoo provided by Taiwan Tsumura, Ltd.

When an epinecidin-1 peptide is used to treat acne caused by *P. acne* infection, it can be formulated for topical administration. Formulations suitable for topical administration include liquid and semi-liquid preparations that can be absorbed by the skin. Examples of liquid and semi-liquid preparations include, but are not limited to, topical solutions, liniments, lotions, creams, ointments or pastes, gels, and emugels.

Topical solutions are homogeneous mixtures prepared by dissolving one or more active agents in a solvent. The solutions may contain other cosmeceutically acceptable chemicals to buffer, stabilize, or preserve the active agents. Solvents commonly used for preparation of topical solutions are ethanol, water, glycerol, propylene glycol, or any other vehicles known in the art. Optionally, L-menthol can be added to a topical solution.

Lotions, a preferred formulation for treating large body area, are typically liquid or semiliquid preparations in which solid particles, including an active agent, are present in a water or alcohol base. They are usually suspensions of solids, and preferably, contains a liquid oily emulsion of the oil-in-water type. The insoluble matter in a lotion should be finely divided such that it applies to the skin surface without friction. Lotions typically contain suspending agents to produce better dispersions as well as compounds useful for localizing and holding the active agent in contact with the skin, e.g., methylcellulose, sodium carbozymethyl-cellulose, or the like.

Creams are viscous liquid or semisolid emulsions, either oil-in-water or water-in-oil, containing cream bases. The cream bases are water-washable and contain an oil phase, an emulsifier, and an aqueous phase. The oil phase, also called the "internal phase," is generally comprised of petrolatum and a fatty alcohol such as cetyl or stearyl alcohol. The aqueous phase usually, although not necessary, exceeds the oil phase in volume, and contains a humectant. The emulsifier in a cream formulation can be a nonionic, anionic, cationic, or amphoteric surfactant. Exemplary surfactants include sorbitan esters or polyoxyethylene derivatives thereof (e.g., polyoxyethylene fatty acid esters) and carboxypolymethylene derivatives (e.g., carbopol).

Ointments are semisolid preparations that are typically based on petrolatum or other petroleum derivatives. The specific ointment base should possess a number of desirable features appreciable by those skilled in the art, e.g., emolliency or the like. As with other carrier or vehicles, an ointment based should be inert, stable, nonirritating, and nonsensitizing. There are four types of suitable ointment bases: oleaginous bases, emulsifiable bases, emulsion bases, and water-soluble bases. See Remington: The Science and Practice of Pharmacy, $19^{th}$ Ed., at pages 1399 and 1404. Oleaginous ointment bases include, for example, vegetable oils, fats obtained from animals, and semidolid hydrocarbons obtained from petroleum. Emusifiable ointment bases, also known as absorbent ointment bases, contain little or no water and include, for example, hydroxystearin sulfate, anhydrous lanolin, and hydrophilic petrolatum. Emulsion ointment bases are either water-in-oil emulsions or oil-in-water emulsions, and include, but are not limited to, cetyl alcohol, glyceryl monostearate, lanolin, and stearic acid. Preferred water-soluble ointment bases are prepared from polyethylene glycols of varying molecular weight.

Pastes are semisolid dosage forms in which an active agent is suspended in a suitable base. Depending on the nature of the base, pastes are divided between fatty pastes and those made from single-phase aqueous gels. The base in a fatty paste is generally petrolatum or hydrophilic petrolatum of the like. The pastes made from single-phase aqueous gels generally incorporate carboxymethylcellulose or the like as a base.

Gels or emugels include a commonly known gel forming agent, such as cellulose derivatives (e.g., methyl cellulose, hydroxyethyl cellulose, and carboxymethyl cellulose), vinyl polymers (e.g., polyvinyl alcohols and polyvinyl pyrrolidones), carboxypoly-methylene derivatives (e.g., carbopol), pectins and gums (e.g., gum arabic and tragacanth, alginate, carrageenate, agar, or gelatin). The gel or emugel formulations may further contain an auxiliary agent commonly known in the art, such as preservative, stabilizer, colorant, or perfume.

The epinecidin-l-peptide-containing topical formulations described above can further include another active agent, such as a vitamin (e.g., vitamin B, 1,25-dihydroxy vitamin D3, vitamin K, vitamin A, and vitamin C), an anti-microbial agent (e.g., tolnaftate, ketoconazole, erythromycin, and tetracycline), an insect-repellent (e.g., aliphatic, cyclic or aromatic amides, citronella oil, terpineol, cineole, neem oil, and ethyl butyacetylaminopropionate), a self-tanning agent (e.g., dihydroacetone and lawsone), an anti-inflammatory agent (e.g., hydrocortisone, prednisone, prednisolone, aspirin, aloe vera, and mixtures thereof), a topical analgesics (e.g., lidocaine, benzocaine, butacaine, and clove oil), a skin redness reducer (e.g., guanidine derivatives or L-arginine derivatives).

To prepare any of the above-mentioned pharmaceutical compositions, the epinecidin-1 or ALF peptide may first require chemical modification to prolong their in vivo half-life. A chemically modified peptide or a peptide analog includes any functional chemical equivalent of the peptide characterized by its increased stability and/or efficacy in vivo or in vitro in respect of the practice of the invention. The term peptide analog also refers to any amino acid derivative of a peptide as described herein. A peptide analog can be produced by procedures that include, but are not limited to, modifications to side chains, incorporation of unnatural amino acids and/or their derivatives during peptide synthesis and the use of cross-linkers and other methods that impose conformational constraint on the peptides or their analogs. Examples of side chain modifications include modification of amino groups, such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with $NABH_4$. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

To facilitate delivery, an epinecidin-1 peptide, an ALF peptide, or a DNA plasmid for expressing the peptide can be conjugated with a chaperone agent. As used herein, "conjugated" means two entities are associated, preferably with sufficient affinity that the therapeutic benefit of the association between the two entities is realized. Conjugated includes covalent or noncovalent bonding as well as other forms of association, such as entrapment of one entity on or within the other, or of either or both entities on or within a third entity (e.g., a micelle).

The chaperone agent can be a naturally occurring substance, such as a protein (e.g., human serum albumin, low-density lipoprotein, or globulin), carbohydrate (e.g., a dextran, pullulan, chitin, chitosan, inulin, cyclodextrin or hyaluronic acid), or lipid. It can also be a recombinant or synthetic molecule, such as a synthetic polyamino acid polymer (e.g., polylysine, poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer, polyethylene glycol, polyvinyl alcohol, polyurethane, poly(2-ethylacryllic acid), N-isopropylacrylamide polymers, and polyphosphazine). Alternatively, the chaperone agent is a micelle, liposome, nanoparticle, or microsphere, in which an epinecidin-1 peptide, an ALF peptide, or its encoding DNA plasmid is encapsulated.

In one example, a chaperone agent serves as a substrate for attachment of one or more of a fusogenic agent, a condensing agent, or a targeting agent.

A fusogenic agent is responsive to the local pH. For instance, upon encountering the pH within an endosome, it can cause a physical change in its immediate environment (e.g., a change in osmotic properties, which disrupts or increases the permeability of the endosome membrane), thereby facilitating release of a peptide or DNA plasmid into host cell's cytoplasm. A preferred fusogenic agent changes charge, for example, becoming protonated at a pH lower than a physiological range (e.g., at pH 4.5-6.5). Fusogenic agents can be molecules containing an amino group capable of undergoing a change of charge (e.g., protonation) when exposed to a specific pH range. Such fusogenic agents include polymers that contain polyamino chains (e.g., polyethyleneimine) and membrane disruptive agents (e.g., mellittin). Other examples include polyhistidine, polyimidazole, polypyridine, polypropyleneimine, mellitin, and a polyacetal substance (e.g., a cationic polyacetal).

A condensing agent interacts with (e.g., attracts, holds, or binds to) a peptide or DNA plasmid and causes it to condense (e.g., reducing the size of the peptide/plasmid), thus protecting the peptide/plasmid against degradation. Preferably, the condensing agent includes a moiety (e.g., a charged moiety) that interacts with the peptide or the DNA plasmid via, e.g., ionic interactions. Examples of the condensing agent include a polylysine, spermine, spermidine, polyamine or quarternary salt thereof, pseudopeptide-polyamine, peptidomimetic polyamine, dendrimer polyamine, arginine, amidine, protamine, cationic lipid, cationic porphyrin, and an alpha helical peptide.

A targeting agent binds specifically to cells infected with trichomonas, propionibacterium, or yeast. When conjugated to an epinecidin-1 peptide, an ALF peptide, or its encoding DNA plasmid, it directs the peptide/plasmid to the target cells mentioned above so as to improve the efficacy of treatment. In one example, the targeting group is an antibody that recognizes a Trichomonas-, Propionibacterium-, or yeast-specific antigen.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. The publications cited herein are incorporated by reference.

Example 1

Treating *T. vaginalis* Infection with Peptides Epinecidin-$1_{22-42}$ and SALF$_{55-76}$ Peptide Epinecidin-$1_{22-42}$, having an amidated C-terminus, was synthesized by Genesis Biotech (Taipei, Taiwan). See Pan et al., Peptides 30:1058-1068 (2009). This peptide has a purity greater than 95%. Linear peptide ls-SALF$_{55-76}$ and cyclic peptide cs-SALF$_{55-76}$, were synthesized following the method described in Pan et al., DNA Cell Biol. 26:403-413 (2007). All of the synthetic peptides were dissolved in phosphate-buffered saline (PBS; pH 7.4).

Four *T. vaginalis* strains, ATCC 30001, ATCC 50148, T1, and MRS-1, were cultured following the conditions recommended by American Type Culture Collection or disclosed in Tsai et al., J. Biol. Chem. 277:5153-5162 (2002). $1\times10^4$ cells of each *T. vaginalis* strain were seeded in a well of a 96-well plate and treated with Epinecidin-$1_{22-42}$, ls-SALF$_{55-76}$ or cs-SALF$_{55-76}$ for 1, 4, or 16 hours at various concentrations. The minimum inhibitory concentrations (MICs) of the peptides against these *T. vaginalis* strains were determined by the standard microdilution method described in Pan et al., Int. Immunopharmacol. 7, 687-700 (2007). Table 1 below shows the MICs of the three peptides against certain *T. vaginalis* strains tested in this study.

TABLE 1

Minimum Inhibitory Concentrations of Peptides Epinecidin-$1_{22-42}$, cs-SALF$_{55-76}$, and ls-SALF$_{55-76}$ against *T. vaginalis*

| *T. vaginalis* strains | Minimum Inhibitory Concentration (µg/ml) | | |
|---|---|---|---|
| | cs-SALF$_{55-76}$ | ls-SALF$_{55-76}$ | Epinecidin-$1_{22-42}$ |
| *T. vaginalis* ATCC 30001 | 100 | 100 | 12.5 |
| *T. vaginalis* KYCC 50148 | 200 | 25 | 25 |
| *T. vaginalis* T1 | 100 | 200 | 25 |

*T. vaginalis* cells (4000 cells/well) were co-treated with metronidazole (100 µg/ml) and Epinecidin-$1_{22-42}$ (200 µg/ml), csSALF$_{55-76}$ (200 µg/ml), or 1sSALF$1_{22-42}$ (200 µg/ml) for 16 hours. Both metronidazole and the peptides were dissolved in PBS. The *T. vaginalis* cells were then stained with cold PBS containing 1 µg/ml ethidium bromide (EtBr) and 1 µg/ml acridine orange (AO) for 10 minutes and examined by epifluorescence microscopy. Red color was observed in the nuclei of *T. vaginalis* cells treated with any of the three peptides, but not in the nuclei of untreated cells. This result indicates that the three peptides destroyed the cellular and nuclear membranes of the *T. vaginalis* cells, thereby allowing EtBr and AO to enter into their nuclei.

The effect of the three peptides on morphology of *T. vaginalis* cells was examined by scanning electron microscopy (SEM) and transmission electron microscopy (TEM) as follows. Cells of the ATCC 50148 and T1 strains were cultured in a 96-well cell culture plate ($1\times10^4$ cells/well). The ATCC 50148 cells were treated with Epinecidin-$1_{22-42}$ (100 µg/ml), csSALF$_{55-76}$ (100 µg/ml), or 1sSALF$1_{22-42}$ (200 µg/ml) for 1, 4, and 16 hours and the T1 cells were treated with Epinecidin-$1_{22-42}$ (100 µg/ml), csSALF$_{55-76}$ (200 µg/ml), or 1sSALF$1_{22-42}$ (100 µg/ml) for the same periods. *T. vaginalis* cells treated with PBS were used as a control. The treated cells were then analyzed by SEM. Results thus obtained indicate that the control cells of both ATCC 50148 and T1 exhibited a flagellum shape, while the T1 and ATCC 50148 cells treated with the peptides showed damaged cell membranes and distorted cell shape. A large amount of cell debris was also observed in the peptide-treated cells.

The *T. vaginalis* cells mentioned above were also subjected to TEM analysis as described in Pan et al., DNA Cell Biol. 26:403-413 (2007). Briefly, the ATCC 50148 cells ($2\times10^4$) were treated for 16 hours with Epinecidin-$1_{22-42}$ at a concentration of 150 µg/ml, csSALF$_{55-76}$ at a concentration of 250 mg/ml, and 1sSALF$1_{22-42}$ at a concentration of 150 µg/ml; the T1 cells ($2\times10^4$) were treated for 16 hours with Epinecidin-$1_{22-42}$ at a concentration of 150 µg/ml, csSALF$_{55-76}$ at a concentration of 250 mg/ml, and 1sSALF$1_{22-42}$ at a concentration of 200 µg/ml. *T. vaginalis* cells treated with PBS were used as a control. Morphology of the treated cells was observed using a transmission electron microscope (Hitachi, H-7000, Tokyo, Japan) at 75 kV; see Pan et al., DNA Cell Biol. 26:403-413 (2007). Similar to the results obtained from the SEM analysis described above, the results obtained from this TEM analysis also showed that peptides Epinecidin-$1_{22-42}$, csSALF$_{55-76}$, and 1sSALF$1_{22-42}$ significantly disrupted the intact structure of the *T. vaginalis* cells.

Finally, the numbers of viable *T. vaginalis* cells after peptide treatment were counted following the method described in Ofer et al., Int. J. Parasitol., 38:959-968 (2008). Briefly, cells of ATCC 50148 and T1 were treated with each of the three peptides mentioned above at 25, 50, 100, or 200 µg/ml for 1, 4, and 16 h (overnight), then the viability was analyzed. Cell viability was then determined by the conventional trypan blue exclusion assay. The numbers of viable cells were calculated as described in Fingrut et al., Br. J. Pharmacol. 146: 800-808 (2005) and Ofer et al. No viable cells were observed in ATCC 50148 cells treated with Epinecidin-1$_{22-42}$ at a concentration of 25 µg/ml for one hour and in T1 cells treated with the same peptide at a concentration of 25 µg/ml for four hours. More than 60% T1 cells died after being treated with this peptide at a concentration of 50 µg/ml for one hour. On the other hand, most ATCC 50148 cells died after being treated with either csSALF$_{55-76}$ or 1sSALF1$_{22-42}$ at 50 µg/ml for four hours and most T1 cells died after being treated with either peptide at a concentration of 25 µg/ml for 16 hours.

In sum, the data mentioned above demonstrate that peptides Epinecidin-1$_{22-42}$, csSALF$_{55-76}$, and 1sSALF1$_{22-42}$ significantly inhibit *T. vaginalis* growth, thereby are effective in treating *T. vaginalis* infection.

Example 2

Treating *P. acnes* Infection with Peptide Epinecidin-1$_{22-42}$

*Propionibacterium acnes* (BCRC #10723) cells were cultured under the conditions recommended by Bioresource Collection and Research Centre (BCRC) in Taiwan (see bcrc-.firdi,org.tw:819/bcrc/indexe.htm). Their growth inhibition by Epinecidin-1$_{22-42}$ was determined following the method described in Pan et al., DNA Cell Biol. 26:403-413 (2007). The minimum inhibitory concentration of this peptide against *P. acnes* was 200 µg/ml.

The effect of Epinecidin-1$_{22-42}$ on *P. acnes* morphology was examined by SEM and TEM as follows. BCRC #10723 cells were seeded in a 6-well plate (1×10$^4$ cells per well), cultured for a sufficient period, collected by centrifugation, and re-suspended in PBS to reach an OD$_{550}$ value of 1.0. The bacterial suspension was mixed with a freshly prepared PBS solution containing the peptide at a concentration of 100 µg/ml or PBS as a control. The treated cells were then subjected to SEM and TEMs analysis following the methods described in Lin et al. and Pan et al. As observed under a scanning or transmission electron microscope, the control BCRC #10723 cells exhibited a spindle shape and had an intact and smooth outer membrane, while the peptide-treated bacteria exhibited a broken outer membrane and their intracellular inclusions were found to have effluxed extracellularly. These results indicate that peptide Epinecidin-1$_{22-42}$ destroyed the outer membranes of *P. acnes* cells, thereby inhibiting their growth.

Example 3

Inhibiting *C. albicans* Growth with Peptide Epinecidin-1$_{22-42}$

Cells of *C. albicans* strain BCRC #20511 were cultured following the protocol provided by BCRC. These cells were treated with peptide Epinecidin-1$_{22-42}$ at various concentrations and their growth inhibition was examined following the method disclosed in Pan et al., Int. Immunopharmacol. 7:687-700 (2007). Results thus obtained indicated that Epinecidin-1$_{22-42}$ significantly inhibited *C. albicans* cell growth. The minimum inhibitory concentration of this peptide against *C. albicans* was found to be 25 µg/ml.

The effect of Epinecidin-1$_{22-42}$ (50 µg/ml) on *C. albicans* cell morphology was analyzed by SEM and TEM following the methods mentioned above. Compared to the BCRC #20511 cells treated with PBS, the cells treated with the peptide showed an irregular shape and disrupted outer/intracellular membranes, indicating that the peptide is capable of destroying the membrane structures of *C. albicans* cells.

Example 4

Anti-Bacterial Activity of Personal Hygiene Products Containing Peptide Epinecidin-1$_{22-42}$ The following personal hygiene products (with or without Epinecidin-1$_{22-42}$) were tested as described below to examine their anti-bacterial activity:

(1) F: a vaginal solution provided by Taiwan Tien Liang Biotech Ltd (containing cocamidopropyl betaine, PEG-7 glyceryl cocate, PEG-200 hydrogenated glyceryl palmitate, benzalkonium chloride, methyl paraben, glycerin, and perfume; pH 4.2-4.6);

(2) F+Epi: a mixture of F and Epinecidin-1$_{22-42}$ (3) J: Yu-Jie-Ning body shampoo provided by Taiwan Tsumura, Ltd. (containing cetrimide, chlorhexidine, 0.05% glyconate, isopropyl alcohol, tartrazine, newcoccline, and perfume, pH 5.3)

(4) J+Epi: a mixture of J and Epinecidin-1$_{22-42}$;

(5) N: 1 mg 50% benzalkonium chloride, 2 mg Rewoderm Lis 80, 30 mg glycerin in 1000 ml sterilized water; and (6) N+Epi: a mixture of N and Epinecidin-1$_{22-42}$.

Cells of *Escherichia coli, Paeudomonas aeruginosa, Staphylococcus aureus, Propionibacterium acnes,* or *Candida albican* (1000 cfu) were mixed with one of the hygiene products listed above and the mixtures thus formed (containing Epinecidin-1$_{22-42}$ at a concentration of 1.56, 3.12, 6.25, 12.5, 25, 50, 100, or 200 µg/ml) were placed in a 96-well plate. After being incubated for 16, 24, 48, and 72 hours, the bacterial number in each well was counted. The results indicate that (1) the bacterial numbers in the wells containing F+Epi and N+Epi were much lower than those in the wells containing F and N, respectively, (2) this anti-bacterial activity was dose dependent, and (3) F+Epi exhibited about 50% higher anti-bacterial activity than F 16 hours after treatment.

The anti-bacterial activity of the above-listed hygiene products were also tested in an antibiotic-sensitivity assay (also known as Kirby-Bauer Assay) following routine procedures. Briefly, a filter paper containing 10 µl of each of the hygiene products was placed on top of an agar plate where bacteria grew. Formation of an inhibitory zone on is indicative of anti-bacterial activity. The results obtained from this study show that F+Epi, J+Epi, and N+Epi (all containing 200 µg/ml Epinecidin-1$_{22-42}$) exhibited much higher anti-bacterial activity as compared to F, J, and N, respectively.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for treating infection with a trichomonas, comprising administering to a subject in need thereof an effective amount of an epinecidin-1 peptide or an anti-lipopolysaccharide factor (ALF) peptide, wherein the epinecidin-1 peptide contains GFIFHIIKGLFHAGKMIHGLV (SEQ ID NO:1) and the ALF peptide contains ECKFTVKPYLKRFQVYYKGRMWCP (SEQ ID NO:2).

2. The method of claim 1, wherein the epinecidin-1 peptide is administered to the subject.

3. The method of claim 2, wherein the epinecidin-1 peptide is GFIFHIIKGLFHAGKMIHGLV (SEQ ID NO:1).

4. The method of claim 2, wherein the trichomonas is *T. vaginalis*.

5. The method of claim 4, wherein the epinecidin-1 peptide is GFIFHIIKGLFHAGKMIHGLV (SEQ ID NO:1).

6. The method of claim 1, wherein the ALF peptide is administered to the subject.

7. The method of claim 6, wherein the ALF peptide is ECKFTVKPYLKRFQVYYKGRMWCP (SEQ ID NO:2).

8. The method of claim 7, wherein the ALF peptide is a cyclic molecule.

9. The method of claim 6, wherein the trichomonas is *T. vaginalis*.

10. The method of claim 9, wherein the ALF peptide is ECKFTVKPYLKRFQVYYKGRMWCP (SEQ ID NO:2).

11. A method for treating infection with a propionibacterium, comprising administering to a subject in need thereof an effective amount of an epinecidin-1 peptide, wherein the epinecidin-1 peptide contains GFIFHIIKGLFHAGKMIHGLV (SEQ ID NO:1), the propionibacterium being *P. acnes*.

12. The method of claim 11, wherein the epinecidin-1 peptide is GFIFHIIKGLFHAGKMIHGLV (SEQ ID NO:1).

* * * * *

SEQUENCE LISTING

<160> NUMBER OF SEQ ID NOS: 2

<210> SEQ ID NO 1
<211> LENGTH: 21
<212> TYPE: PRT
<213> ORGANISM: Artificial sequence
<220> FEATURE:
<223> OTHER INFORMATION: A fragment of grouper Epinecidin-1 between
      amino acids 22 and 42

<400> SEQUENCE: 1

Gly Phe Ile Phe His Ile Ile Lys Gly Leu Phe His Ala Gly Lys Met
1               5                   10                  15

Ile His Gly Leu Val
            20

<210> SEQ ID NO 2
<211> LENGTH: 24
<212> TYPE: PRT
<213> ORGANISM: Artificial sequence
<220> FEATURE:
<223> OTHER INFORMATION: A fragment of shrimp ALF between amino acids 55
      and 76

<400> SEQUENCE: 2

Glu Cys Lys Phe Thr Val Lys Pro Tyr Leu Lys Arg Phe Gln Val Tyr
1               5                   10                  15

Tyr Lys Gly Arg Met Trp Cys Pro
            20